US007471385B2

(12) United States Patent
Mestha et al.

(10) Patent No.: US 7,471,385 B2
(45) Date of Patent: Dec. 30, 2008

(54) SYSTEMS AND METHODS FOR SELECTING A REFERENCE DATABASE FOR DETERMINING A SPECTRUM OF AN OBJECT BASED ON FLUORESCENCE OF THE OBJECT

(75) Inventors: Lalit K. Mestha, Fairport, NY (US); Fred F. Hubble, III, Friendswood, TX (US); Kenneth Mihalyov, Webster, NY (US); Tonya L. Love, Rochester, NY (US); Gary W. Skinner, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 303 days.

(21) Appl. No.: 11/033,882

(22) Filed: Jan. 13, 2005

(65) Prior Publication Data

US 2006/0152718 A1  Jul. 13, 2006

(51) Int. Cl.
*G01J 1/10* (2006.01)
*H04N 1/46* (2006.01)

(52) U.S. Cl. .................... 356/243.5; 356/402; 358/500; 358/504

(58) Field of Classification Search ................. 356/300, 356/317, 318, 417; 250/458
See application file for complete search history.

(56) References Cited

U.S. PATENT DOCUMENTS

| | | | |
|---|---|---|---|
| 3,910,701 A | 10/1975 | Henderson et al. | |
| 4,003,660 A | 1/1977 | Christie, Jr. | |
| 4,553,033 A | 11/1985 | Hubble, III et al. | |
| 4,648,051 A | 3/1987 | Wandell et al. | |
| 4,752,827 A | 6/1988 | Cassagne et al. | |
| 4,830,020 A | 5/1989 | Ruth | |
| 4,989,985 A | 2/1991 | Hubble, III et al. | |
| 4,992,963 A | 2/1991 | Funt et al. | |
| 5,078,497 A | 1/1992 | Borton et al. | |
| 5,082,529 A | 1/1992 | Burk | |
| 5,107,332 A | 4/1992 | Chan | |
| 5,137,364 A | 8/1992 | McCarthy | |
| 5,272,518 A | 12/1993 | Vincent | |

(Continued)

FOREIGN PATENT DOCUMENTS

EP    0 491 131 A1    6/1992

(Continued)

OTHER PUBLICATIONS

Lee et al. "Spectral estimation and color appearance prediction of fluorescent materials." Optical Engineering vol. 40, Issue 10, pp. 2069-2076. Oct. 2001.*

(Continued)

*Primary Examiner*—Tarifur Chowdhury
*Assistant Examiner*—Tara S Pajoohi
(74) *Attorney, Agent, or Firm*—Oliff & Berridge, PLC (57) ABSTRACT

To determine the spectra of objects that have different degrees of fluorescence, a plurality of reference databases are provided, each reference database being suited to a different degree of fluorescence. A most appropriate one of the reference databases is selected based on a predicted degree of fluorescence of an object for which a reflectance spectrum is to be determined. The prediction of the degree of fluorescence may be based on user input, or may be predicted by using a priori information, such as a priori knowledge of media types.

18 Claims, 5 Drawing Sheets

U.S. PATENT DOCUMENTS

| | | | |
|---|---|---|---|
| 5,377,000 A | 12/1994 | Berends | |
| 5,386,123 A | 1/1995 | Hubble, III et al. | |
| 5,408,535 A | 4/1995 | Howard, III et al. | |
| 5,420,682 A | 5/1995 | Haggerty et al. | |
| 5,526,190 A | 6/1996 | Hubble, III et al. | |
| 5,537,516 A | 7/1996 | Sherman et al. | |
| 5,543,838 A | 8/1996 | Hosier et al. | |
| 5,550,653 A | 8/1996 | TeWinkle et al. | |
| 5,604,362 A | 2/1997 | Jedlicka et al. | |
| 5,612,902 A | 3/1997 | Stokes | |
| 5,668,596 A | 9/1997 | Vogel | |
| 5,671,059 A | 9/1997 | Vincent | |
| 5,723,517 A | 3/1998 | Campo et al. | |
| 5,748,221 A | 5/1998 | Castelli et al. | |
| 5,748,780 A | 5/1998 | Stolfo | |
| 5,767,980 A | 6/1998 | Wang et al. | |
| 5,790,211 A * | 8/1998 | Seachman et al. | 349/3 |
| 5,805,314 A | 9/1998 | Abe et al. | |
| 5,808,297 A | 9/1998 | Jedlicka et al. | |
| 5,838,451 A | 11/1998 | McCarthy | |
| 5,844,680 A | 12/1998 | Sperling | |
| 5,963,244 A | 10/1999 | Mestha et al. | |
| 5,963,333 A | 10/1999 | Walowit et al. | |
| 5,991,023 A | 11/1999 | Morawski et al. | |
| 6,020,583 A | 2/2000 | Walowit et al. | |
| 6,062,137 A | 5/2000 | Guo et al. | |
| 6,088,095 A * | 7/2000 | Sharma | 356/243.5 |
| 6,118,903 A | 9/2000 | Liu | |
| 6,147,761 A | 11/2000 | Walowit et al. | |
| 6,157,454 A | 12/2000 | Wagner et al. | |
| 6,157,469 A | 12/2000 | Mestha | |
| 6,178,007 B1 | 1/2001 | Harrington | |
| 6,198,536 B1 | 3/2001 | Baker | |
| 6,252,679 B1 | 6/2001 | Wang | |
| 6,263,291 B1 | 7/2001 | Shakespeare et al. | |
| 6,272,440 B1 * | 8/2001 | Shakespeare et al. | 702/85 |
| 6,304,294 B1 | 10/2001 | Tao et al. | |
| 6,333,501 B1 | 12/2001 | Labrenz | |
| 6,351,308 B1 | 2/2002 | Mestha | |
| 6,373,568 B1 | 4/2002 | Miller et al. | |
| 6,449,045 B1 | 9/2002 | Mestha | |
| 6,467,867 B1 | 10/2002 | Worthington et al. | |
| 6,480,299 B1 | 11/2002 | Drakopoulos et al. | |
| 6,556,300 B2 | 4/2003 | Tandon et al. | |
| 6,556,932 B1 | 4/2003 | Mestha et al. | |
| 6,567,170 B2 | 5/2003 | Tandon et al. | |
| 6,584,435 B2 | 6/2003 | Mestha et al. | |
| 6,587,793 B2 | 7/2003 | Viassolo et al. | |
| 6,603,551 B2 | 8/2003 | Mestha et al. | |
| 6,621,576 B2 | 9/2003 | Tandon et al. | |
| 6,633,382 B2 | 10/2003 | Hubble, III et al. | |
| 6,721,692 B2 | 4/2004 | Mestha et al. | |
| 6,754,279 B2 | 6/2004 | Zhou et al. | |
| 6,917,443 B1 | 7/2005 | Wang | |
| 2003/0009293 A1 | 1/2003 | Anderson et al. | |
| 2003/0050768 A1 | 3/2003 | Mestha et al. | |
| 2003/0055575 A1 * | 3/2003 | Viassolo et al. | 702/27 |
| 2003/0055611 A1 | 3/2003 | Mestha et al. | |
| 2003/0157504 A1 | 8/2003 | Chee et al. | |
| 2004/0218174 A1 * | 11/2004 | Natori | 356/318 |

FOREIGN PATENT DOCUMENTS

| | | |
|---|---|---|
| EP | 0 582 997 A1 | 2/1994 |
| EP | 0 625 847 A1 | 11/1994 |
| EP | 0 811 829 A2 | 12/1997 |
| EP | 0 868 074 A1 | 9/1998 |
| EP | 0 915 615 A2 | 5/1999 |
| JP | A-10-304216 | 11/1998 |
| JP | A-2001-235371 | 8/2001 |
| WO | WO 97/34409 A2 | 9/1997 |

OTHER PUBLICATIONS

U.S. Appl. No. 10/758,096, filed Jan. 16, 2004, Mestha et al.

Lee, B-K and Shen, F-C.: *Spectral estimation and color appearance prediction of fluorescent materials*, Optical Engineeringvol. 40 No. 10, Oct. 2001.

Chang, G-W and Chen, Y-C.: *Spectral estimation of color CCD cameras*, SPI Conference for Input/Output and Imaging Technology, Taipei, Taiwan, Jul. 1998. SPIC vol. 3422.

Lin, T-N, and Shu, J.: *A Color Consistency Algorithm Between Different Printers*, Proceeding of Conference of the Society for Imaging Science and Technology. May 17-20, pp. 409-411.

* cited by examiner

SYSTEMS AND METHODS FOR SELECTING A REFERENCE DATABASE FOR DETERMINING A SPECTRUM OF AN OBJECT BASED ON FLUORESCENCE OF THE OBJECT

INCORPORATION BY REFERENCE

Cross-reference and incorporation by reference are made to the following commonly assigned U.S. patent applications and/or the following U.S. patents: U.S. Pat. No. 6,584,435; U.S. Pat. No. 6,587,793; U.S. Pat. No. 6,556,932; U.S. Pat. No. 6,449,045; U.S. Pat. No. 6,556,300; U.S. Pat. No. 6,567,170; U.S. Pat. No. 6,633,382; U.S. Pat. No. 6,621,576; U.S. Pat. No. 6,603,551; U.S. Pat. No. 6,721,692; U.S. patent application Ser. No. 10/758,096, entitled "Reference Database And Method For Determining Spectra Using Measurements From An Led Color Sensor, And Method Of Generating A Reference Database"; and co-pending application entitled "Systems and Methods for Augmenting Spectral Range of an LED Spectrophotometer."

BACKGROUND

Automatic in-line color calibration systems can be much more effective with an in-line color measurement system where a spectrophotometer may be mounted in the paper path of the moving copy sheets in the printer, preferably in the output path after fusing or drying, without having to otherwise modify the printer, or interfere with or interrupt normal printing, or the movement of the printed sheets in said paper path, and yet provide accurate color measurements of test color patches printed on the moving sheets as they pass the spectrophotometer. That enables a complete closed loop color control of a printer.

A typical spectrophotometer gives color information in terms of measured reflectances or transmittances of light, at the different wavelengths of light, from the test surface. This spectrophotometer desirably provides distinct electric signals corresponding to the different levels of reflected light received from the respective different illumination wavelength ranges or channels.

Known devices capable of providing distinct electric signals corresponding to the different levels of reflected light received from the respective different illumination wavelength ranges or channels include a grating-based spectrophotometer made by Ocean Optics Inc., LED based sensors marketed by "ColorSavvy" or Accuracy Microsensor; and other spectrophotometers by Gretag MacBeth (Viptronic), ExColor, and X-Rite (DTP41). However, those devices are believed to have significant cost, measurement time, target displacement errors, and/or other difficulties, for use in real-time printer in-line measurements.

As used herein, unless otherwise specifically indicated, the term "spectrophotometer" may encompass a spectrophotometer, colorimeter, and densitometer, as broadly defined herein. The definition or use of such above terms may vary or differ among various scientists and engineers. However, the following is an attempt to provide some simplified clarifications relating and distinguishing the respective terms "spectrophotometer," "calorimeter," and "densitometer," as they may be used in the specific context of specification examples of providing components for an in-line color printer color correction system, but not necessarily as claim limitations.

A typical "spectrophotometer" measures the reflectance of an illuminated object of interest over many light wavelengths. Typical prior spectrophotometers in this context use 16 or 32 channels measuring from 380 nm to 730 nm or so, to cover the humanly visible color spectra or wavelength range. A typical spectrophotometer gives color information in terms of measured reflectances or transmittances of light, at the different wavelengths of light, from the test surface. (This is to measure more closely to what the human eye would see as a combined image of a broad white light spectra image reflectance, but the spectrophotometer desirably provides distinct electrical signals corresponding to the different levels of reflected light from the respective different illumination wavelength ranges or channels.)

A "calorimeter" normally has three illumination channels, red, green and blue. That is, generally, a "colorimeter" provides its three (red, green and blue or "RGB") values as read by a light sensor or detector receiving reflected light from a color test surface sequentially illuminated with red, green and blue illuminators, such as three different color LEDs or one white light lamp with three different color filters. It may thus be considered different from, or a limited special case of, a "spectrophotometer," in that it provides output color information in the trichromatic quantity known as RGB.

Trichromatic quantities may be used for representing color in three coordinate space through some type of transformation. Other RGB conversions to "device independent color space" (i.e., RGB converted to conventional L*a*b*) typically use a color conversion transformation equation or a "lookup table" system in a known manner.

A "densitometer" typically has only a single channel, and simply measures the amplitude of light reflectivity from the test surface, such as a developed toner test patch on a photoreceptor, at a selected angle over a range of wavelengths, which may be wide or narrow. A single illumination source, such as an IR LED, a visible LED, or an incandescent lamp, may be used. The output of the densitometer detector is programmed to give the optical density of the sample. A densitometer of this type is basically "color blind." For example, a cyan test patch and magenta test patch could have the same optical densities as seen by the densitometer, but, of course, exhibit different colors.

SUMMARY

A multiple LED reflectance spectrophotometer, as in the examples of the embodiments herein, may be considered to belong to a special class of spectrophotometers which normally illuminate the target with multiple instances of narrow band or monochromatic light. Others, with wide band illumination sources, can be flashed Xenon lamp spectrophotometers, or incandescent lamp spectrophotometers. A spectrophotometer is normally programmed to give more detailed reflectance values by using more than 3 channel measurements (for example, 10 or more channel measurements), with conversion algorithms. That is in contrast to normal three channel calorimeters, which cannot give accurate, human eye related, reflectance spectra measurements, because they have insufficient measurements for that (only 3 measurements).

It is desirable for a printer color control system to dynamically measure the color of test patches on the printed output media "in line", that is, while the media is still in the sheet transport or paper path of a print engine, for real-time and fully automatic printer color correction applications.

For a low cost implementation of the color sensor, a multiple illuminant device is used as the illumination source, and has, for example, 8, 10, 12 or 16 LEDs. Each LED is selected to have a narrow band response curve in the spectral space. Therefore, for example, ten LEDs would correspond to ten measurements in the reflectance curve. The LEDs, or other multiple illuminant based color sensor equivalent, e.g., lasers, are switched on one at a time as, for example, the measured media is passed through a transport of a printer. The reflected light is then detected by a photodetector and the corresponding voltage integrated and normalized with a white tile.

To obtain a smooth curve similar to that of a Gretag spectrophotometer, linear or cubic spline algorithms could be used, which blindly interpolate the data points without knowledge of the color space. Unfortunately, due to lack of measurements at wavelengths below 430 nm and above 660 nm (due to lack of LEDs at these wavelengths), extrapolation with 10 measurements can lead to errors.

U.S. Pat. No. 6,584,435, U.S. Pat. No. 6,587,793, U.S. Pat. No. 6,556,932, and U.S. Pat. No. 6,449,045 collectively disclose various systems and methods for using the integrated sensor measurements to determine a fully populated reflectance spectra with reflectance values at specific wavelengths. Those methods and systems use a reference database in determining the spectra, and convert integrated multiple illuminant measurements from a non-fully illuminant populated color sensor into a fully populated spectral curve. As described collectively in these disclosures, the reference database is generated by measuring the reflectance spectra of some set of reference colors, with an accurate reference spectrophotomer, such as a Gretag spectrophotometer, and their corresponding LED sensor outputs, with the sensor array of a given color measuring device. In general, the more densely populated the database is, i.e., the more reference colors used, the better the resulting accuracy. Furthermore, even spacing of the reference colors in the color space gives greater accuracy. The data stored in the reference database will be referred to hereafter as the training samples.

U.S. patent application Ser. No. 10/758,096 relates to a reference database usable with the above-described systems, and a method for constructing the reference database, and a method of using the reference database to obtain a spectral curve. According to the disclosure of U.S. patent application Ser. No. 10/758,096, the database may be partitioned into a plurality of clusters, and an appropriate centroid may be determined for each cluster. The centroids may be obtained by, for example, vector quantization. The training samples may be assigned to the clusters by comparing the Euclidean distance between the centroids and the sample under consideration, and assigning each sample to the cluster having the centroid with the shortest Euclidean distance. When all training samples have been assigned, the resulting structure is stored as the reference database.

When reconstructing the spectra for new measurements from the sensor, the Euclidean distances between actual color samples under measurement and each cluster centroid are calculated. The spectra may then be reconstructed using only the training samples from the cluster corresponding to the shortest Euclidean distance. By thus using only a limited number of the total training samples, the speed and accuracy of the spectral reconstruction is enhanced.

However, when determining the spectra of objects that have different degrees of fluorescence, errors can occur, as described in more detail below. "Fluorescence," as used in this application, is defined as the phenomenon in which absorption, by an object, of light of a given wavelength results in emission, from the object, of light of a different wavelength. Typically, the different wavelength is a longer wavelength. As defined in this application, it will be understood that all objects have a "degree of fluorescence," but that this degree may be high, low, or zero.

The training samples typically used in constructing a reference database for spectral reconstruction have a low degree of fluorescence, or zero degree of fluorescence. This is acceptable for many applications, because many objects to be measured (i.e., objects for which a spectrum is to be reconstructed) also have a low degree low degree of fluorescence, or zero degree of fluorescence. However, if such a reference database is used to measure objects having a medium degree of fluorescence or a high degree of fluorescence, errors can result. If the multiple illuminants, such as LEDs, used in the color sensor include an LED that emits a wavelength within the fluorescence excitation range, then these errors can be at least partially compensated by, for example, a method disclosed in co-pending application entitled "Systems and Methods for Augmenting Spectral Range of an LED Spectrophotometer," Attorney Docket No. D/A3073.

However, the fluorescence excitation range is from about 350 nm to about 410 nm for many fluorescent objects, such as fluorescent paper, and as discussed above, multiple illuminant color sensors may lack LEDs or other illuminants for wavelengths below 430 nm and above 660 nm. To add one or more LEDs or other illuminants for the fluorescence excitation range would increase the cost of the color sensor.

An option that does not require an extra illuminant is to provide different reference databases for different degrees of fluorescence. In embodiments, this invention provides different reference databases for different degrees of fluorescence which are obtained during a sensor characterization process, and allows selection of an appropriate one of the reference databases based on a predicted degree of fluorescence of the object to be measured. The prediction may be based on user input, e.g., by the user selecting a degree of fluorescence at a user interface. Alternatively, the prediction may be based on historical patterns present in similar contexts of the object. For example, in the context of printing, if a certain type of print job always uses paper of a predetermined fluorescence, then the fluorescence may be predicted based on the programmed print job.

These and other objects, advantages and salient features of the invention are described in or apparent from the following description of exemplary embodiments.

BRIEF DESCRIPTION OF THE DRAWINGS

Exemplary embodiments will be described with reference to the drawings, wherein like numerals represent like parts, and wherein.

DETAILED DESCRIPTION OF EMBODIMENTS

A spectrophotometer according to the invention is preferably a spectrophotometer especially suitable for being mounted at the printed side of a sheet output path of a color printer to optically evaluate color imprinted output sheets as they move past the spectrophotometer, variably spaced therefrom, without having to contact the sheets or interfere with the normal movement of the sheets. In particular, it may be used to measure a number of color test patch samples printed by the printer on actual printed sheet output of the printer during regular or selected printer operation intervals (between normal printing runs or print jobs). These color test sheet printing intervals may be at regular timed intervals, and/or at each machine "cycle-up," or as otherwise directed by the system software. The spectrophotometer may be mounted at one side of the paper path of the machine, or, if it is desired to use duplex color test sheets, two spectrophotometers may be mounted on opposite sides of the paper path.

Relatively frequent color calibration of a color printer is highly desirable, since the colors actually printed on the output media (as compared to the colors intended to be printed) can significantly change, or drift out of calibration over time, for various known reasons. For example, changes in the selected or loaded print media, such as differences paper or plastic sheet types, materials, weights, calendaring, coating, humidity, etc., or changes in the printer's ambient conditions, changes in the image developer materials, aging or wear of printer components, varying interactions of different colors being printed, etc. Printing test color patches on test sheets of the same print media under the same printing conditions during the same relative time periods as the color print job being color-controlled is thus very desirable.

It is thus also advantageous to provide dual-mode color test sheets, in which multiple color patches of different colors are printed on otherwise blank areas of each, or selected, banner, cover, or other inter-document or print job separator sheets. Different sets of colors may be printed on different banner or other test sheets. This dual use of such sheets saves both print paper and printer utilization time, and also provides frequent color calibration opportunities where the printing system is one in which banner sheets are being printed at frequent intervals anyway.

An additional feature which can be provided is to tailor or set the particular colors or combinations of the test patches on a particular banner or other test sheet to those colors which are about to be printed on the specific document for that banner sheet, i.e., the document pages which are to be printed immediately subsequent to that banner sheet (the print job identified by that banner sheet). This can provide a "real time" color correction for the color printer which is tailored to correct printing of the colors of the very next document to be printed.

It will be appreciated that these test patch images and colors may be automatically sent to the printer imager from a stored data file specifically designed for printing the dual mode banner sheet or other color test sheet page, and/or they may be embedded inside the customer job containing the banner page. That is, the latter may be directly electronically associated with the electronic document to be printed, and/or generated or transmitted by the document author or sender. Because the printed test sheet color patches colors and their printing sequence is known (and stored) information, the in-line spectrophotometer measurement data therefrom can be automatically coordinated and compared.

After the spectrophotometer or other color sensor reads the colors of the test patches, the measured color signals may be automatically processed inside the system controller or the printer controller to produce or modify the tone reproduction curve, as explained in the cited references. The color test patches on the next test sheet may then be printed with that new tone reproduction curve. This process may be repeated so as to generate further corrected tone reproduction curves. If the printer's color image printing components and materials are relatively stable, with only relatively slow long term drift, and there is not a print media or other abrupt change, the tone reproduction curve produced using this closed loop control system will be the correct curve for achieving consistent colors for at least one or even a substantial number of customer print jobs printed thereafter, and only relatively infrequent and few color test sheets, such as the normal banner sheets, need be printed.

In addition to use in printers, it should be noted that color measurements, and/or the use of color measurements for various quality or consistency control functions, are also important for many other different technologies and applications, such as in the production of textiles, wallpaper, plastics, paint, inks, food products, etc. and in the measurement or detection of various properties of various materials, objects or substances. Thus, the invention may have applications in various such other fields where these materials, objects or substances are to be color tested, including both (1) applications in which color measurements are taken and applied in a closed loop control system and (2) applications in which the measurement result is not fed back into a control loop, but is used to generate a one-time output.

Figure 1:
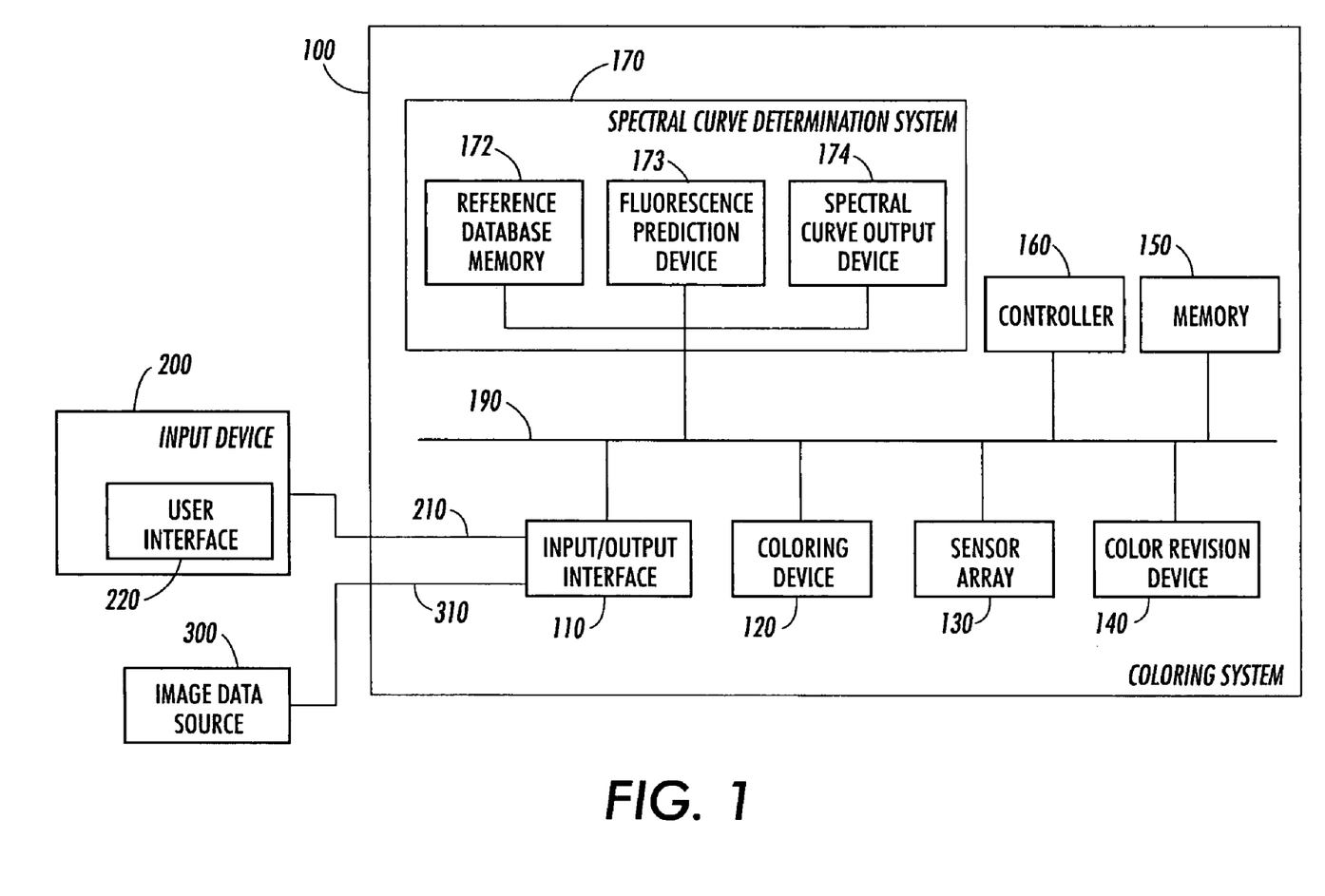
FIG. 1 is a functional block diagram illustrating an exemplary coloring system according to the invention.

FIG. 1 is a functional block diagram illustrating an exemplary embodiment of a coloring system 100 according to this invention. The coloring system 100 is connected to an input device 200 via a link 210. The input device 200 inputs various information needed to implement the operations of the coloring system 100, as described in more detail below, and may include a mouse, a keyboard, a touch-screen input device, a voice recognition-based input device, and/or any other known or later developed device usable for inputting information. The input device 200 preferably includes a user interface 220, described in detail below, although some embodiments may not require the user interface 220. Alternatively, the user interface 220 may be part of the coloring system 100 itself, and, e.g., may be connected directly to the bus 190 of the coloring system 100.

The coloring system 100 optionally is connected to an image data source 300 via a link 310. The connection to the image data source 300 is "optional" because it is required only for certain embodiments of the coloring system 100.

For example, when the coloring system 100 is a marking device, such as a printer, the image data source 300 is required. However, when the coloring system 100 is a system for performing a coloring operation that does not require image data, the image data source 300 is not required. An example of a coloring operation that may not require image data is an operation of making a colored food product such as cereal or the like.

The image data source 300 can be a digital camera, a scanner, or a locally or remotely located computer, or any other known or later developed device that is capable of generating electronic image data. Similarly, the image data source 300 can be any suitable device that stores and/or transmits electronic image data, such as a client or a server of a network. The image data source 300 can be integrated with the coloring system 100, as in a digital copier having an integrated scanner. Alternatively, the image data source 300 can be connected to the coloring system 100 over a connection device, such as a modem, a local area network, a wide area network, an intranet, the Internet, any other distributed processing network, or any other known or later developed connection device.

It should also be appreciated that, while the electronic image data can be generated at the time of printing an image from an original physical document, the electronic image data could have been generated at any time in the past. Moreover, the electronic image data need not have been generated from the original physical document, but could have been created from scratch electronically. The image data source 300 is thus any known or later developed device which is capable of supplying electronic image data over the link 310 to the coloring system 100. The link 310 can thus be any known or later developed system or device for transmitting the electronic image data from the image data source 300 to the coloring system 100.

Further, it should be appreciated that the links 210 and 310 can be a wired, wireless or optical link to a network (not shown). The network can be a local area network, a wide area network, an intranet, the Internet, or any other distributed processing and storage network.

The coloring system 100 includes a coloring device 120, a sensor array 130, a color revision device 140, a memory 150, a controller 160 and a spectral curve determination system 170, which are interconnected by a data/control bus 190. The spectral curve determination system 170 includes a reference database memory 172, a fluorescence prediction device 173 and a spectral curve output device 174.

The coloring device 120 may be, for example, a print engine/printing head or marking engine/marking head, when the coloring system 100 is a printer or other marking device. The coloring device 120 may be, for example, a colorant dispenser that dispenses a colorant onto an object or into a mixture. U.S. Pat. No. 6,603,551, incorporated herein by reference in its entirety, discusses various applications for color measurement and/or adjustment, including textiles and/or textile manufacturing, and the coloring system 100 may, for example, be applied in any of these applications. Thus, the coloring device 120 may be any known or later developed device that directly or indirectly controls the final appearance of an object, material or substance.

The sensor array 130 includes multiple illuminants, such as LEDs, lasers or the like, arranged around a central photodetector (not shown), or arranged in correspondence to a plurality of photodetectors or photosites as described in, for example, U.S. Pat. No. 6,556,300, U.S. Pat. No. 6,567,170, U.S. Pat. No. 6,633,382 and/or U.S. Pat. No. 6,621,576. The illuminants will be referred to hereafter as LEDs for convenience. The number of LEDs may be any number greater than three, when a single photosensor is used, or may be as low as two when multiple photosites or photosensors are used. A larger number of LEDs gives greater accuracy, but it costs more to include more LEDs, and thus there are practical limits to the number of LEDs included in the sensor array 130, especially since an object of this invention is to provide a low-cost spectrophotometer. Therefore, the number of LEDs is preferably from about 8 to about 16.

Each LED is selected to have a narrow band response curve in the visible range of the spectral space. Therefore, for example, ten LEDs would correspond to ten measurements in the reflectance curve. The LEDs, or other multiple illuminant based color sensor equivalent, e.g., lasers, are switched on one at a time as, for example, the measured media is passed through a transport of a printer. The reflected light is then detected by the photodetector and the corresponding voltage integrated and normalized with a white tile. The normalization is preferably performed during each measurement. For the normalization, use of a white tile calibration look-up table, which is stored in memory 150, is a standard practice in the color measurement industry. When the white tile calibration look-up table is used, the detector output is normalized to between 0 to 1 in accordance with, for example, the following equation:

$$V_{m_i} = (V_i - V_i^o) R_i^w / (V_i^{fs} - V_i^o), \quad (1)$$

where $V_i^o$ is the black measurement sensing system offset of the $i^{th}$ LED, $V_i^{fs}$ is the white tile measurement, $V_i$ is the sensor detector output, and $R_i^w$ is the reflectance spectral value of the white tile at the mean wavelength of the $i^{th}$ LED, or at a wavelength at which LED intensities are at their peak values. Any other known or later developed method for normalization may alternatively be used. $V_{m_i}$ may be compensated for temperature variation.

The color revision device 140 calibrates the output of the coloring device 120 in accordance with information obtained from the spectral curve output device 174 of the spectral curve determination system 170. This calibration may be performed as often as necessary or desired to maintain a desirable output of the coloring device 120.

The memory 150 may serve as a buffer for information coming into or going out of the coloring system 100, may store any necessary programs and/or data for implementing the functions of the coloring system 100, and/or may store data at various stages of processing. The above-mentioned white tile lookup table may be stored in the memory 150 if desired. The reference database memory 172, described in more detail below, may also be part of the memory 150 if desired. Furthermore, it should be appreciated that the memory 150, while depicted as a single entity, may actually be distributed. Alterable portions of the memory 150 are, in various exemplary embodiments, implemented using static or dynamic RAM. However, the memory 150 can also be implemented using a floppy disk and disk drive, a writeable optical disk and disk drive, a hard drive, flash memory or the like. The generally static portions of the memory 150 are, in various exemplary embodiments, implemented using ROM. However, the static portions can also be implemented using other non-volatile memory, such as PROM, EPROM, EEPROM, an optical ROM disk, such as a CD-ROM or DVD-ROM, and disk drive, flash memory or other alterable memory, as indicated above, or the like.

The controller 160 controls the operation of other components of the coloring system 100, performs any necessary calculations and executes any necessary programs for implementing the processes of the coloring system 100 and its individual components, and controls the flow of data between other components of the coloring system 100 as needed.

The spectral curve determination system 170 determines and outputs spectral curves. Specifically, the spectral curve output device 174 outputs spectral curves based on a plurality of spectra which are determined by the controller 160 based on information from the reference database memory 172 and information from the fluorescence prediction device 173, which are described in more detail below, and the output of the sensor array 130 from different color targets.

To obtain an output similar to that of a reference spectrophotometer, such as a Gretag spectrophotometer, it is necessary to convert the readings from the sensory array 130 to reflectance spectra. A Gretag spectrophotometer outputs 36 spectral reflectance values, evenly spaced at 10 nm over the visible spectrum (e.g., 380 nm to 730 nm). Therefore, in the following examples, the readings from the sensor array 130 are converted to 36 reflectance values. In other words, when there are 8 LEDs in the sensor array 130, the LEDs are sequentially actuated, readings (typically voltage readings) are collected from the photodetector for each respective LED actuation, and the 8 readings (voltages) from the sensor array 130 are converted to 36 reflectance values per color. If a multiple photosite sensor is used, it will be appreciated that a desired number of outputs, for example 8 outputs, will be obtained from smaller number of LEDs, for example 3 or 4 LEDs. An X-Rite spectrophotometer has 31 outputs evenly spaced at 10 nm over the spectrum of 400 nm to 700 nm, so in the case of an X-Rite spectrophotometer the readings from the sensor array 130 are converted to 31 reflectance values.

It will be understood that each of the circuits shown in FIG. 1, e.g., the color revision device 140, the controller 160, the fluorescence prediction device 173 and the spectral curve output device, or portions of any of these, can be implemented as portions of a suitably programmed general purpose computer. Alternatively, each of the circuits shown in FIG. 1 can be implemented as physically distinct hardware circuits within an ASIC, or using a FPGA, a PDL, a PLA or a PAL, or using discrete logic elements or discrete circuit elements. The particular form each of the circuits shown in FIG. 1 will take is a design choice and will be obvious and predictable to those skilled in the art.

Figure 2:
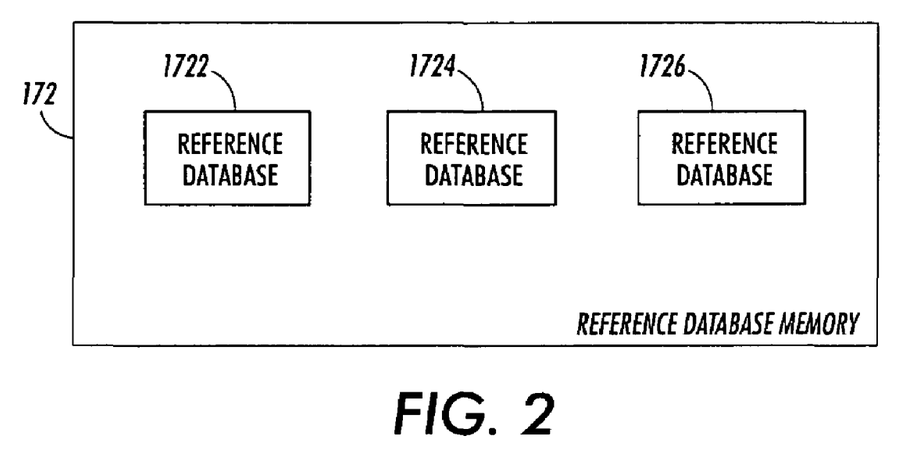
FIG. 2 illustrates an exemplary reference database memory that stores a plurality of reference databases.

FIG. 2 shows that a plurality of reference databases 1722, 1724 and 1726 are stored in the reference database memory 172. Each of the reference databases 1722, 1724 and 1726 is designed for a different level of fluorescence; thus, the reference databases 1722, 1724 and 1726 collectively accommodate measurement of objects at three different levels of fluorescence. Of course, more reference databases may be provided to accommodate more levels of fluorescence, and some embodiments may only have two reference databases to accommodate only two levels of fluorescence.

Each reference database 1722, 1724 and 1726 is generated by measuring the reflectance spectra of some set of reference colors, with an accurate reference spectrophotometer, such as a Gretag spectrophotometer, and their corresponding LED sensor outputs, with the sensor array 130. For each reference database, the reference colors are measured from an object having a different fluorescence. For example, to generate the reference database 1722, reference colors may be printed on paper having low fluorescence, or no fluorescence, and then the reflectance spectra of these reference colors may be measured with the reference spectrophotometer, and the corresponding LED sensor outputs with respect to the reference colors may be measured with the sensor array 130. To generate the reference database 1724, the same reference colors used to generate the reference database 1722 may be printed on paper having a medium fluorescence, and then the reflectance spectra of these reference colors may be measured with the reference spectrophotometer, and the corresponding LED sensor outputs with respect to the reference colors may be measured with the sensor array 130. Similarly, to generate the reference database 1726, the same reference colors used to generate the reference databases 1722 and 1724 may be printed on paper having a high fluorescence, and then the reflectance spectra of these reference colors may be measured with the reference spectrophotometer, and the corresponding LED sensor outputs with respect to the reference colors may be measured with the sensor array 130. Although printing colors on sheets of paper has been described as an example, there are other possible applications, such as applying paint or other colorant to objects or surfaces of different fluorescence.

In general, the more densely populated the database is, i.e., the more reference colors used, the better the resulting accuracy. In one exemplary reference database, about 5000 colors are used. Furthermore, even spacing of the reference colors in the color space gives greater accuracy. The data stored in the reference databases 1722, 1724 and 1726 will be referred to hereafter as the training samples.

The sensor transfer function, i.e., the information included in the reference databases 1722, 1724 and 1726, is a mapping from reflectance spectra (as measured by a reference spectrophotometer) to sensor outputs (as measured by the sensor array 130) formed by a set of N spectra to voltage measurements, denoted as $$\Omega=[S_1\,S_2\ldots S_N]\in R^{n\times N}\to V=[V_1\,V_2\ldots V_N]\in R^{l\times N} \quad (2)$$

where $S_1\,S_2\ldots S_N$ are the vector elements containing the N spectral curves, each curve containing 36 elements, i.e., reflectance values (n=36), and $V_1\,V_2\ldots V_N$ are the vector elements from the LED sensor outputs (in volts), each having eight components (l=8) when an 8-LED spectrophotomer is used. Here, each curve contains 36 elements because a Gretag spectrophotometer, which outputs 36 values, is used. If a different spectrophotometer is used which has a different number of outputs, n will be a correspondingly different number. $V_1\,V_2\ldots V_N$ are each a vector including 8 normalized voltages corresponding to the 8 LED color sensor outputs for a given color. R indicates the set of real numbers. N is a predetermined number based on certain color gamut specifications for the color sensor array 130. Generally, the larger the gamut, the larger will be N. As an example, N may be about 5000.

The value of l discussed above depends on the number of sensor outputs, which may be the number of illuminants, e.g., the number of LEDs. However, it will be appreciated that when a multiple photosite sensor is used, l will not be equal to the number of LEDs.

For greater accuracy, each of the reference databases 1722, 1724 and 1726 may be partitioned into cells using, e.g., the techniques described in U.S. patent application Ser. No. 10/758,096.

Figure 3:
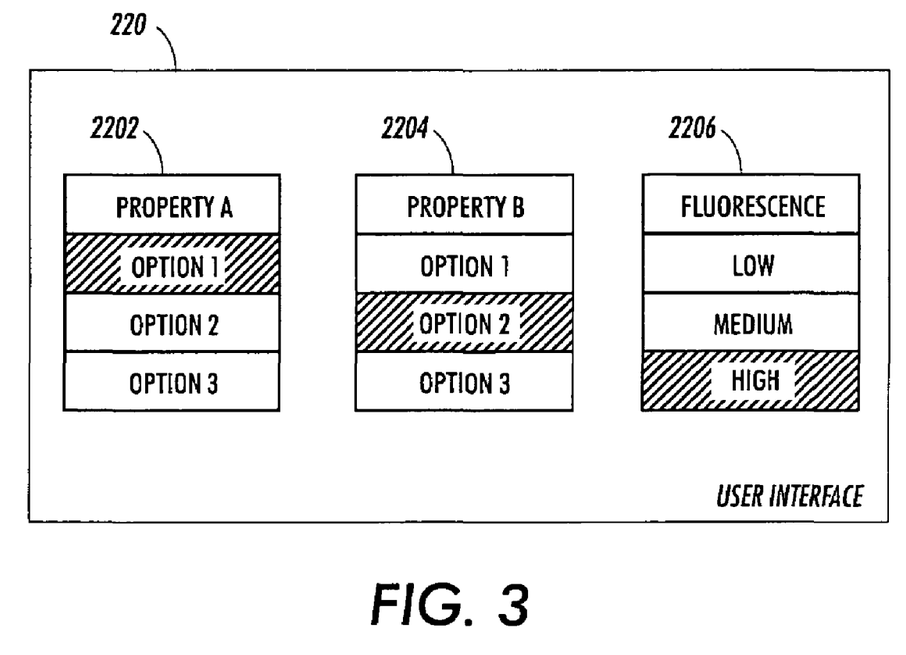
FIG. 3 illustrates a first exemplary user interface that enables a user to indicate a degree of fluorescence.

FIG. 3 illustrates an example of the user interface 220. The user interface 220 is a touch screen interface; however, it will be appreciated that any other type of user interface, such as a mouse, key pad, voice-activated input device, or the like, or any combination of these, is also acceptable. The user interface 220 may include selection menus 2202, 2204 to enable the user to select properties, such as properties of paper in a paper tray of a printer or the like. Paper color, paper weight, paper coating, or the like are examples of properties that may be selected by the selection menus 2202 and 2203. The user interface 220 includes a fluorescence selection menu 2206 that enables the user to select the fluorescence of the paper or other object that is to be measured. In this example, the user may make a qualitative selection from among "low" fluorescence, "medium" fluorescence, and "high" fluorescence options. In FIG. 2, the shaded boxes show options that have been selected. Thus, for Property A in selection menu 2202, "Option 1" has been selected; for Property B in selection menu 2202, "Option 2" has been selected; and in the fluorescence selection menu 2202, "High" has been selected.

Figure 4:
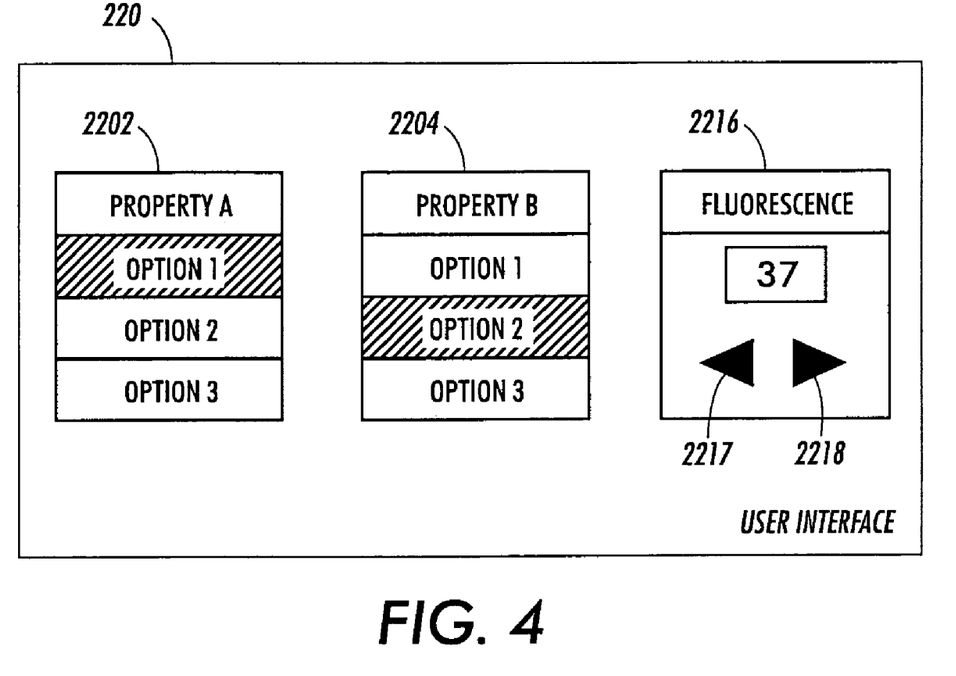
FIG. 4 illustrates a second exemplary user interface that enables a user to indicate a degree of fluorescence.

FIG. 4 illustrates another example of the user interface 220. In this example, the user may make a quantitative selection of the degree of fluorescence by pushing decrease button 2217 or increase button 2218. In FIG. 4, a quantitative value of "37" has been selected as the degree of fluorescence.

The fluorescence prediction device 173 (FIG. 1) predicts the degree of fluorescence of the object or objects to be measured. This prediction may be based on information received via the user interface 220, e.g., the quantitative or qualitative fluorescence information described above in connection with FIGS. 3-4, or may be based on calculations performed inside the device to appropriately modify or select the value of fluorescence based on a priori knowledge of the media types, or some other type of information usable for prediction of a degree of fluorescence. One example of another type of such information is historical patterns present in similar contexts of the object. For example, in the context of printing, if a certain type of print job always uses paper of a predetermined fluorescence, then the fluorescence may be predicted based on the programmed print job.

The prediction of the degree of fluorescence by the fluorescence prediction device 173 determines which of the plurality of reference databases 1722, 1724 and 1726 will be used by the spectral curve output device 174. After the most appropriate reference database has been selected, the coloring system 100 may operate using the output of the sensor array 130 and, e.g., an algorithm for determining spectra. Exemplary algorithms for determining spectra are described in U.S. Pat. No. 6,721,692, and in U.S. Pat. No. 6,584,435, U.S. Pat. No. 6,587,793, and U.S. patent application Ser. No. 10/758,096, entitled "Reference Database And Method For Determining Spectra Using Measurements From An Led Color Sensor, And Method Of Generating A Reference Database," each of which is incorporated herein by reference in its entirety.

Figure 5:
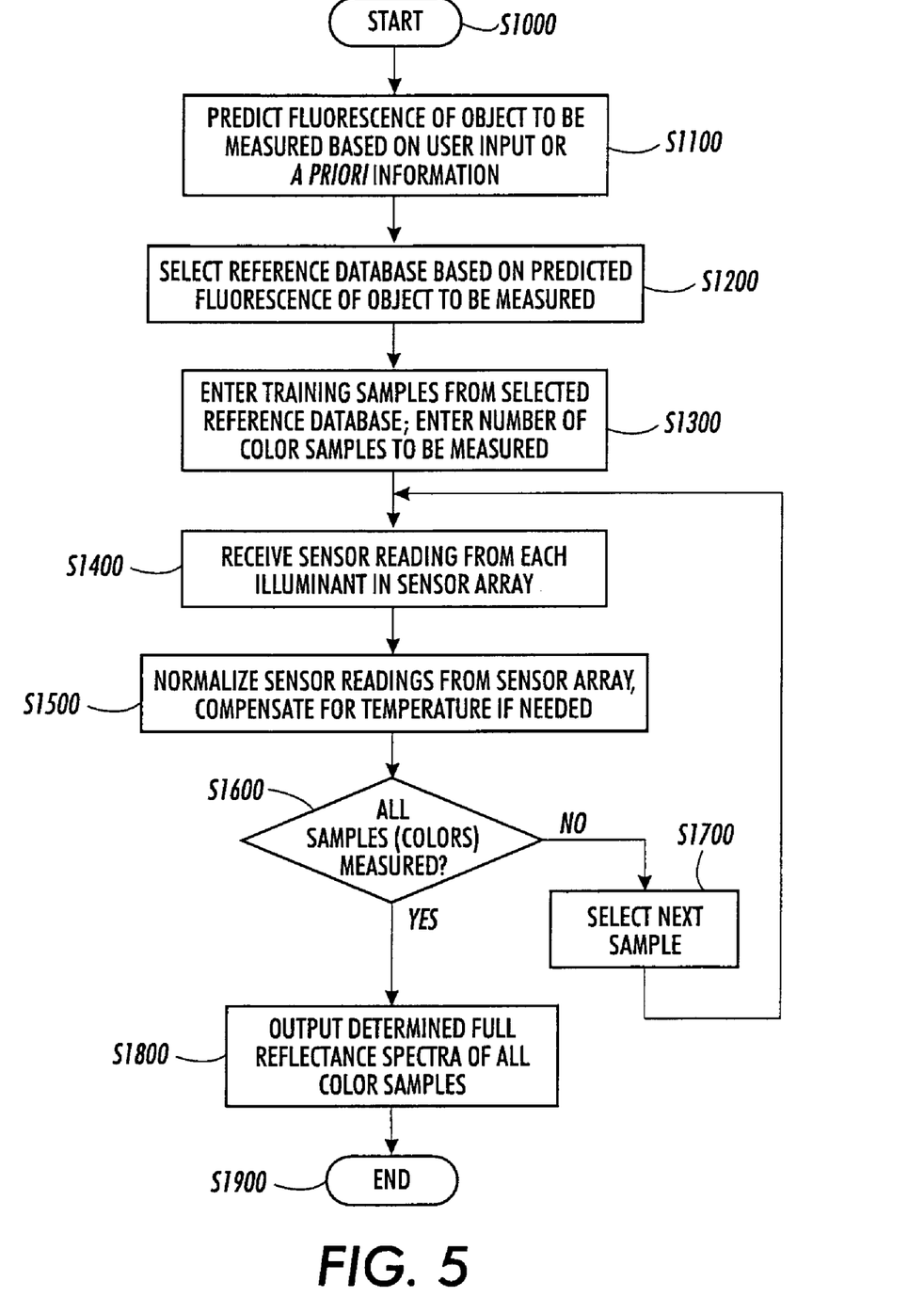
FIG. 5 is a flowchart illustrating an exemplary method of determining spectra.

FIG. 5 is a flowchart illustrating an exemplary method of determining spectra. Beginning in step S1000, the process continues to step S1100, where a prediction is made of the degree of fluorescence of the object to be measured. Next, in step S1200, an appropriate reference database is selected based on the degree of fluorescence predicted in step S1100. Then, in step S1300, the training samples from the selected reference database are entered, and the number of color samples to be measured is entered. Next, in step S1400, a sensor reading is received from each illuminant in a sensor array. Continuing to step S1500, the sensor readings are normalized, and compensated for temperature if necessary or desired. It should be appreciated that steps S1300 through S1500 are similar to steps performed in, for example, methods described in the above-referenced U.S. Pat. No. 6,721, 692, and/or other ones of the documents incorporated by reference above. The process then continues to step S1600.

In step S1600, it is determined whether all color samples have been measured. If not all the color samples have been measured, the process continues to step S1700. Otherwise, the process jumps to step S1800.

In step S1700, the next color sample is selected. Steps S1400-S1600 are then repeated. When all color samples have been measured, the process goes to step S1800 and outputs the full reflectance spectra, i.e., the spectral curve, of the color samples. Finally, the process ends in step S1900.

It will be appreciated that if only a single color sample is to be measured, steps S1600 and S1700 are not necessary, and that only a single reflectance spectrum will be output.

Figure 6:
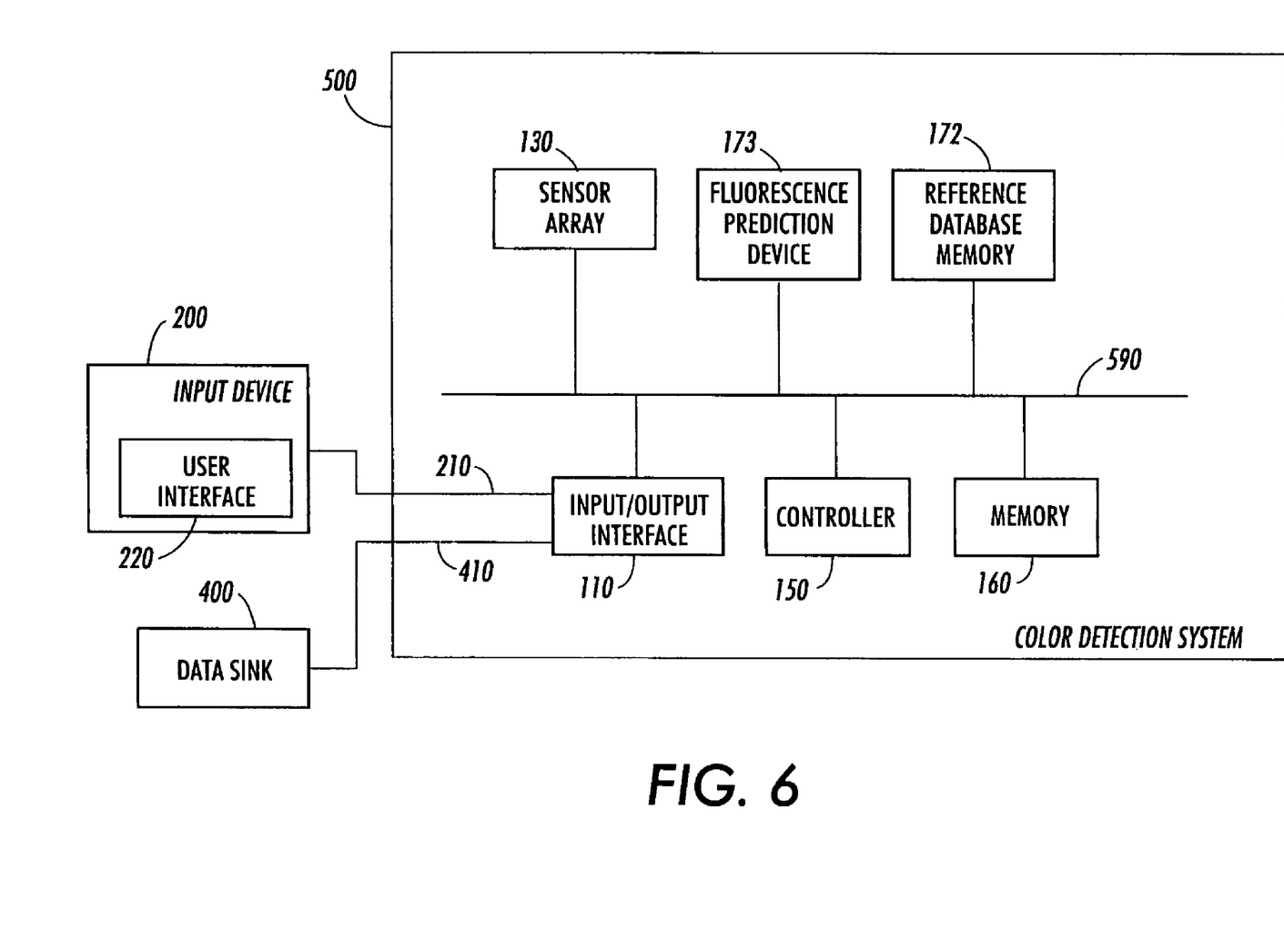
FIG. 6 is a functional block diagram illustrating an exemplary embodiment of a color detection system according to this invention.

FIG. 6 is a functional block diagram illustrating an exemplary embodiment of a color detection system 500 according to this invention. The color detection system 500 includes an input/output interface 110, a sensor array 130, a controller 150, a memory 160, a reference database memory 172, and a fluorescence prediction device 173, which may be identical to the corresponding elements of FIG. 1, interconnected by a data/control bus 590. The color detection system 500 is connected to a user input device 200 via a link 210, similar to the input device 200 and link 210 described above in conjunction with FIG. 1. The user input device 200 may include a user interface 220 that, like the user interface 220 described above, allows a user to indicate a degree of fluorescence. The color detection system 500 is also connected to a data sink 400 via a link 410 which, like the links 210 and 310, can be a wired, wireless or optical link to a network (not shown). In general, the data sink 400 can be any device that is capable of outputting or storing the processed data generated by the color detection system, such as a printer, a copier or other image forming devices, a facsimile device, a display device, a memory, or the like.

The color detection system 500 may be, or be included in, a portable or stationary unit designed specifically to measure color of a target object. In use, the fluorescence prediction device 173 is activated, preferably by user input via the user interface 220, to obtain a predicted degree of fluorescence. The controller 150 selects an appropriate reference database from the reference database memory 172 based on the predicted fluorescence. The color detection system 500 is positioned with the sensor array 130 facing the target object, the sensor array 130 is activated as described above, and then the above-described algorithm is executed by the controller 150, using data from the sensor array 130 and the selected reference database, to obtain an estimated spectrum of the target object. The estimated spectrum is then output to the data sink 400.

From the foregoing descriptions, it can be appreciated that, in embodiments, the invention may provide a calibration tool for scanners, printers, digital photocopiers, etc., and that, in embodiments, the invention may provide a color measurement tool designed to provide one-time color measurements of target objects.

The coloring system 100 of FIG. 1 and the color detection system 500 of FIG. 6 are preferably implemented either on a single program general purpose computer or separate programmed general purpose computers, with an associated sensor array 130 (and coloring device 120, in the case of FIG. 1). However, the coloring system 100 and color detection system 500 can also be implemented on a special purpose computer, a programmed micro-processor or micro-controller and peripheral integrated circuit element, an ASIC or other integrated circuit, a digital signal processor, a hard-wired electronic or logic circuit such as a discrete element circuit, a programmable logic device such as a PLD, PLA, FPGA, PAL, or the like. In general, any device capable of implementing a finite state machine that is in turn capable of implementing the flowcharts shown in FIG. 5, or appropriate portions thereof, can be used to implement the spectral curve reconstruction device according to this invention.

Furthermore, the disclosed methods may be readily implemented in software using object or object-oriented software development environments that provide portable source code that can be used on a variety of computer or workstation hardware platforms. Alternatively, appropriate portions of the disclosed coloring system 100 and the color detection system 500 may be implemented partially or fully in hardware using standard logic circuits or a VLSI design. Whether software or hardware is used to implement the systems in accordance with this invention is dependent on the speed and/or efficiency requirements of the system, the particular function, and the particular software or hardware systems or microprocessor or microcomputer systems being utilized. The processing systems and methods described above, however, can be readily implemented in hardware or software using any known or later developed systems or structures, devices and/or software by those skilled in the applicable art without undue experimentation from the functional description provided herein together with a general knowledge of the computer arts.

Moreover, the disclosed methods may be readily implemented as software executed on a programmed general purpose computer, a special purpose computer, a micro-processor, or the like. In this case, the methods and systems of this invention can be implemented as a routine embedded on a personal computer or as a resource residing on a server or workstation, such as a routine embedded in a photocopier, a color photocopier, a printer driver, a scanner, or the like. The systems and methods can also be implemented by physical incorporation into a software and/or hardware system, such as the hardware and software system of a photocopier or a dedicated image processing system.

While the invention has been described in conjunction with the specific embodiments described above, these embodiments should be viewed as illustrative and not limiting. Various changes, substitutes, improvements or the like are possible within the spirit and scope of the invention.

What is claimed is:

1. A method of determining a reflectance spectrum, comprising:
   predicting a degree of fluorescence of an object, prior to determining a reflectance spectrum of the object;
   selecting a most appropriate reference database from among a plurality of reference databases based on the predicted degree of fluorescence of the object, each reference database being designed for a different level of fluorescence, and each reference database indicating a reflectance spectra of a set of reference colors, and corresponding sensor outputs;
   determining a reflectance spectrum of the object using the most appropriate database; and
   using the determined reflectance spectrum to evaluate output of a coloring device.

2. The method of claim 1, wherein predicting the degree of fluorescence comprises:
   presenting a user interface that includes an option to select a degree of fluorescence; and
   using the degree of fluorescence selected by the user as the predicted degree of fluorescence.

3. The method of claim 2, wherein the user interface allows the user to make a qualitative selection of the degree of fluorescence.

4. The method of claim 2, wherein the user interface allows the user to make a quantitative selection of the degree of fluorescence.

5. The method of claim 1, wherein predicting the degree of fluorescence comprises referring to a priori information.

6. The method of claim 5, wherein the a priori information comprises a priori knowledge of a media type of a medium that bears the object.

7. A computer-readable storage medium on which is recorded a program that causes a computer to implement the method of claim 1.

8. A spectral determination system, comprising:
   a plurality of illuminants;
   at least one photodetector that detects light originating from the plurality of illuminants and reflected by an object;
   a controller that:
      predicts a degree of fluorescence of the object, prior to a determining a reflectance spectrum of the object;
      selects a most appropriate reference database from among a plurality of reference databases based on the predicted degree of fluorescence of the object, each reference database being designed for a different level of fluorescence, and each reference database indicating a reflectance spectra of a set of reference colors, and corresponding sensor outputs; and
      determines a spectrum of the object based on the illuminant sensor outputs and the most appropriate reference database.

9. The system of claim 8, further comprising a user interface that includes an option to select a degree of fluorescence, wherein predicting the degree of fluorescence comprises using the degree of fluorescence selected by the user as the predicted degree of fluorescence.

10. The system of claim 9, wherein the user interface allows the user to make a qualitative selection of the degree of fluorescence.

11. The system of claim 9, wherein the user interface allows the user to make a quantitative selection of the degree of fluorescence.

12. The system of claim 8, wherein predicting the degree of fluorescence comprises referring to a priori information.

13. The system of claim 12, wherein the a priori information comprises a priori knowledge of a media type of a medium that bears the object.

14. A coloring system incorporating the spectral determination system of claim 8.

15. The coloring system of claim 14, wherein the coloring system is one of a digital photocopier and a color printer.

16. The coloring system of claim 14, wherein the coloring system is a xerographic color printer.

17. The coloring system of claim 14, wherein the coloring system is an ink-jet printer.

18. A color detection system incorporating the spectral determination system of claim 8.

* * * * *